United States Patent
Park et al.

(10) Patent No.: US 9,347,133 B2
(45) Date of Patent: May 24, 2016

(54) METHOD OF DEPOSITING A RUTHENIUM METAL THIN FILM OR RUTHENIUM OXIDE THIN FILM

(75) Inventors: Jung Woo Park, Seoul (KR); Jun Young Kim, Jeonju (KR); Kwang deok Lee, Jeollabuk-do (KR); Whee Won Jin, Seoul (KR)

(73) Assignee: HANSOL CHEMICAL CO., LTD., Wanju-Gun, Jeollabuk-Do (KR)

( * ) Notice: Subject to any disclaimer, the term of this patent is extended or adjusted under 35 U.S.C. 154(b) by 30 days.

(21) Appl. No.: 14/351,930

(22) PCT Filed: Mar. 30, 2012

(86) PCT No.: PCT/KR2012/002390
§ 371 (c)(1),
(2), (4) Date: Sep. 29, 2014

(87) PCT Pub. No.: WO2013/058451
PCT Pub. Date: Apr. 25, 2013

(65) Prior Publication Data
US 2015/0050431 A1    Feb. 19, 2015

(30) Foreign Application Priority Data
Oct. 20, 2011  (KR) .................. 10-2011-0107659
Mar. 13, 2012  (KR) .................. 10-2012-0025377

(51) Int. Cl.
*C23C 16/06* (2006.01)
*C23C 16/16* (2006.01)
*C23C 16/18* (2006.01)
*C23C 16/455* (2006.01)
*C07F 17/02* (2006.01)

(52) U.S. Cl.
CPC ........... *C23C 16/45553* (2013.01); *C07F 17/02* (2013.01); *C23C 16/18* (2013.01)

(58) Field of Classification Search
CPC ........ C23C 16/06; C23C 16/14; C23C 16/18; C23C 16/45553; C23C 16/16
See application file for complete search history.

(56) References Cited

U.S. PATENT DOCUMENTS

| 8,404,306 B2 * | 3/2013 | Dussarrat ................ C23C 16/18 427/250 |
| 8,753,718 B2 * | 6/2014 | Dussarrat ................ C23C 16/18 427/248.1 |
| 2010/0221577 A1 * | 9/2010 | Dussarrat ................ C23C 16/18 428/702 |

FOREIGN PATENT DOCUMENTS

WO    WO 2008/078296    *  7/2008

OTHER PUBLICATIONS

Van der Drift, Robert C., et al., "Ruthenium-Catalyzed Isomerization of Allylic Alcohols: Oxidation State Determines Resistance Against Diene Inhibition". Eur. J. Inorg. Chem. 2002, 2147-2155.*
Keijsper, Jan, et al., "Ruthenium Carbonyl 1,4-Diaza-1,3-butadiene (R-DAB) Reaction Sequence". Inorg. Chem. 1985, 24, 518-525.*
International Preliminary Report on Patentability for application No. PCT/KR2012/002390, issued Apr. 22, 2014.
Written Opinion for application No. PCT/KR2012/002390, mailed Oct. 23, 2012.

* cited by examiner

*Primary Examiner* — Bret Chen
(74) *Attorney, Agent, or Firm* — Hauptman Ham, LLP

(57) ABSTRACT

A method of depositing a ruthenium metal thin film or ruthenium oxide thin film comprising a ruthenium compound used for depositing metallic Ru or $RuO_2$ thin film on a substrate via atomic layer deposition, and the ruthenium compound represented by Chemical Formula 1, wherein L is a ligand selected from the group consisting of 1-ethyl-1,4-cyclohexadiene, 1,3-butadiene, and isoprene.

[Chemical Formula 1]

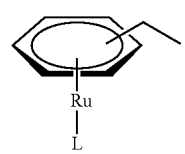

6 Claims, 6 Drawing Sheets

METHOD OF DEPOSITING A RUTHENIUM METAL THIN FILM OR RUTHENIUM OXIDE THIN FILM

CROSS REFERENCE TO RELATED APPLICATION

This application claims the priority of Korean Patent Application No. 10-2011-0107659, filed on Oct. 20, 2011 and No. 10-2012-0025377, filed on Mar. 13, 2012 in the KIPO (Korean Intellectual Property Office). Further, this application is the National Phase application of International Application No. PCT/KR2012/002390 filed Mar. 30, 2012, which designates the United States and was published in Korean.

TECHNICAL FIELD

The present invention relates to a ruthenium compound including a specific ligand structure of 1-ethyl-1,4-cyclohexadiene, 1,3-butadiene or isoprene and having superior thermal stability, vaporizing property and step coverage, and a thin film deposited using same.

BACKGROUND ART

Ruthenium is a metal having superior thermal and chemical stability. Owing to high work function, easy etching and easier thin film formation as compared to other metals such as Pt, Ir, etc., it is promising as an electrode material of a next-generation memory device. Also, ruthenium has good conductivity with a specific resistance of 7.1-7.6 $\mu\Omega\cdot$cm and ruthenium oxide is capable of improving leakage current characteristics because of low specific resistance of about 40 $\mu\Omega\cdot$cm and high work function of 4.7-4.9 eV.

As precursors for the preparation of ruthenium metal or ruthenium oxide thin films, $(\eta^6$-arene$)(\eta^4$-diene)Ru [Giovanni Vitulli et al., *Inorganics Chimica Acta*, vol. 149, 1988, 235-239]; (toluene)Ru(COD), (toluene)Ru(norbonadiene), etc. [International Patent Application Publication No. WO 2008/044478]; (1,3-cyclohexadienyl)(4-isopropyl-1-methylbenzene)Ru, etc. as (diene)(Rbenzene)ruthenium, or the like are known. Although these precursors are liquid at room temperature and have vapor pressure favorable for formation of ruthenium thin films, the process window is narrow during thin film formation under continuous heating. In particular, since step coverage is poor when depositing ruthenium or ruthenium oxide thin film on a substrate having a trench structure with a specific aspect ratio, they are inapplicable to large-scale production.

Korean Patent Application Publication No. 2010-60482 discloses a ruthenium precursor compound having high thermal stability and high vapor pressure whose properties are not degraded even under continuous heating. Korean Patent Publication No. 2010-60482 discloses a ruthenium compound having a cyclic alkene group of 3-8 carbon atoms having 1-4 double bond(s) as a ligand (L) and describes (1,5-cyclooctadienyl)(ethylbenzene)ruthenium represented by Chemical Formula A as a specific example of the compound.

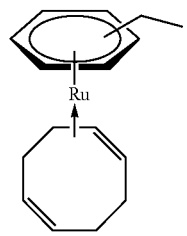

[Chemical Formula A]

Korean Patent Application Publication No. 2010-60482 describes that the ruthenium compound represented by Chemical Formula A is solid at room temperature with a melting point of 24-25° C. and the precursor exhibits superior thermal stability and vaporizing property, with $T_{1/2}$ of 247° C. in thermogravimetric analysis (TGA) and showing constant weight loss without decomposition in the temperature range of 80-150° C. However, according to Korean Patent Publication No. 2010-60482, the precursor having the ligand introduced vaporizes quickly with few residues on a substrate in the deposition temperature range of 130-160° C. and preparation of high-purity thin film has not been demonstrated.

The inventors of the present invention have prepared a ruthenium precursor compound having a specific ligand introduced, which shows $T_{1/2}$ of 230° C. in thermogravimetric analysis (TGA), less than 1.5% of residue rate and superior thermal stability with constant weight loss without decomposition of the precursor in the temperature range of 80-120° C. and fast vaporization and few residues of the precursor in the temperature range of 130-160° C. In particular, the precursor compound exhibits superior step coverage when forming a ruthenium thin film through atomic layer deposition (ALD).

DISCLOSURE

Technical Problem

The present invention is directed to providing a ruthenium compound including 1-ethyl-1,4-cyclohexadiene, 1,3-butadiene or isoprene as a specific ligand and having superior thermal stability, vaporizing property and step coverage.

The present invention is also directed to providing a ruthenium metal thin film or a ruthenium oxide thin film grown by atomic layer deposition (ALD) using the ruthenium compound and a method for depositing the thin film.

Technical Solution

In an aspect, the present invention provides a ruthenium compound represented by Chemical Formula 1:

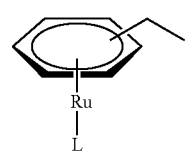

[Chemical Formula 1]

wherein L is a ligand selected from 1-ethyl-1,4-cyclohexadiene, 1,3-butadiene or isoprene.

Advantageous Effects

A ruthenium compound of the present invention is liquid at room temperature and has high vapor pressure.

Since the ruthenium compound of the present invention has superior thermal stability, atomic layer deposition (ALD) can be conducted at higher temperatures without concern of contamination due to thermal decomposition.

In addition, the ruthenium compound of the present invention can be grown into a ruthenium thin film or a ruthenium oxide having high step coverage by atomic layer deposition.

BEST MODE FOR CARRYING OUT THE INVENTION

Figure 1:
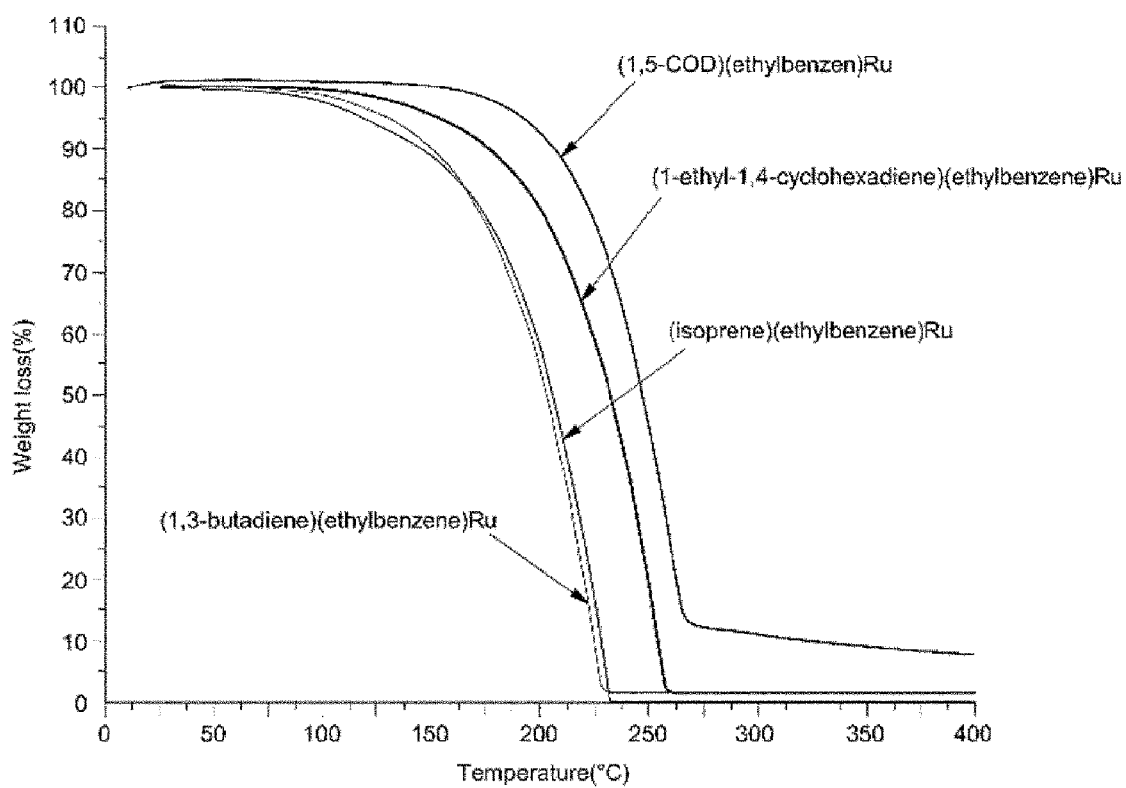
FIG. 1 shows thermogravimetric analysis (TGA) spectra of ruthenium compounds of Examples 1, 2 and 3, showing the rate of weight loss versus temperature.
Figure 2A:
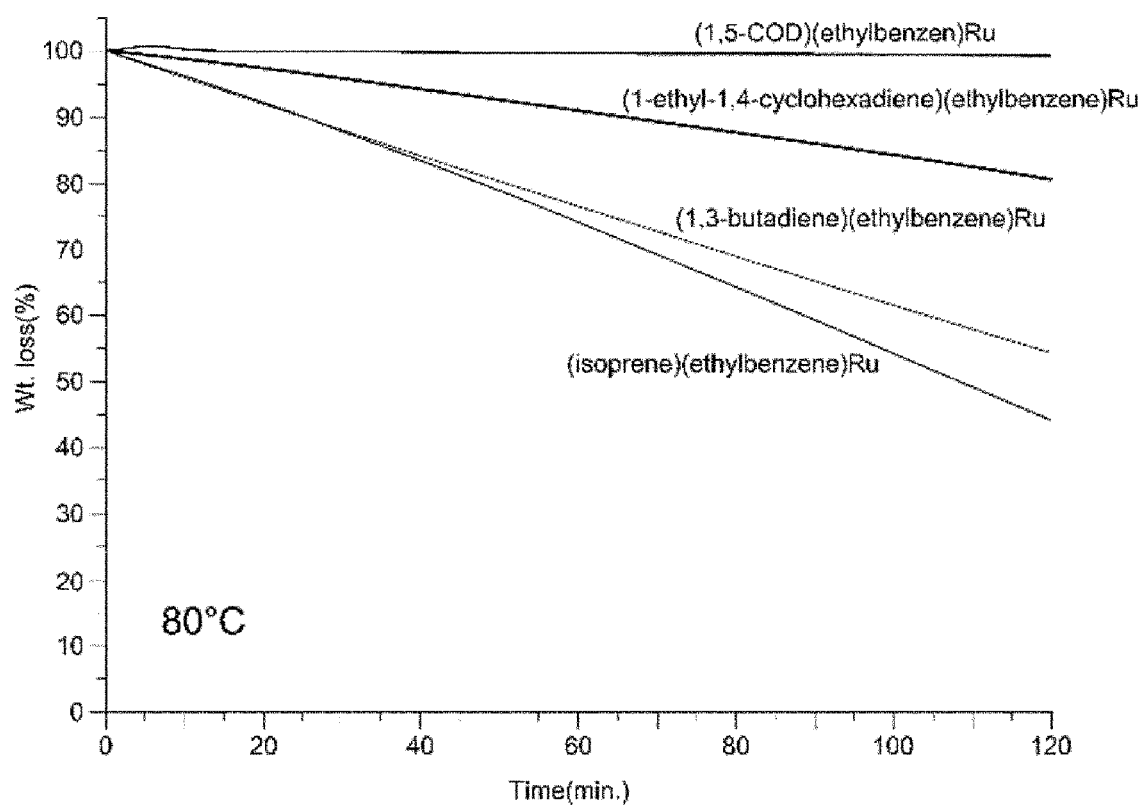
FIGS. 2a, 2b, 2c and 2d show isothermal TGA spectra of (1-ethyl-1,4-cyclohexadienyl)(ethylbenzene)ruthenium at 80° C., 100° C., 120° C. and 150° C., showing the rate of weight loss versus time.
Figure 2B:
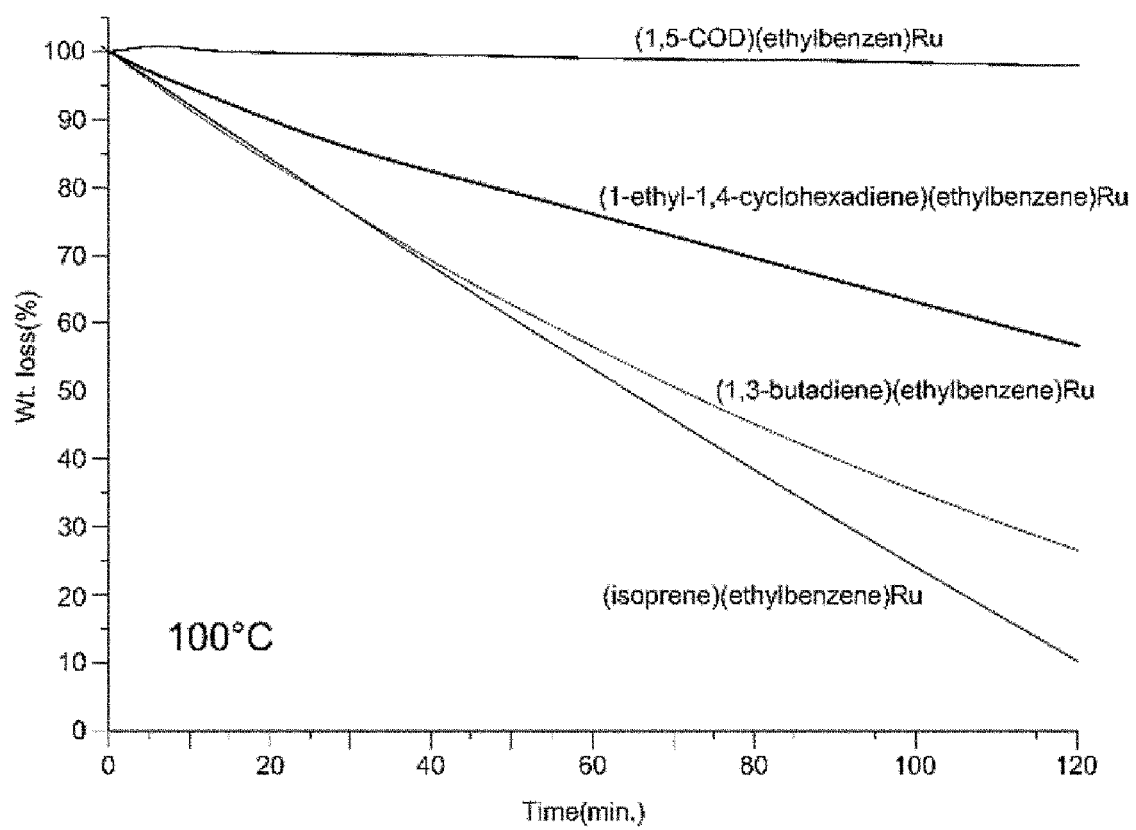
Figure 2C:
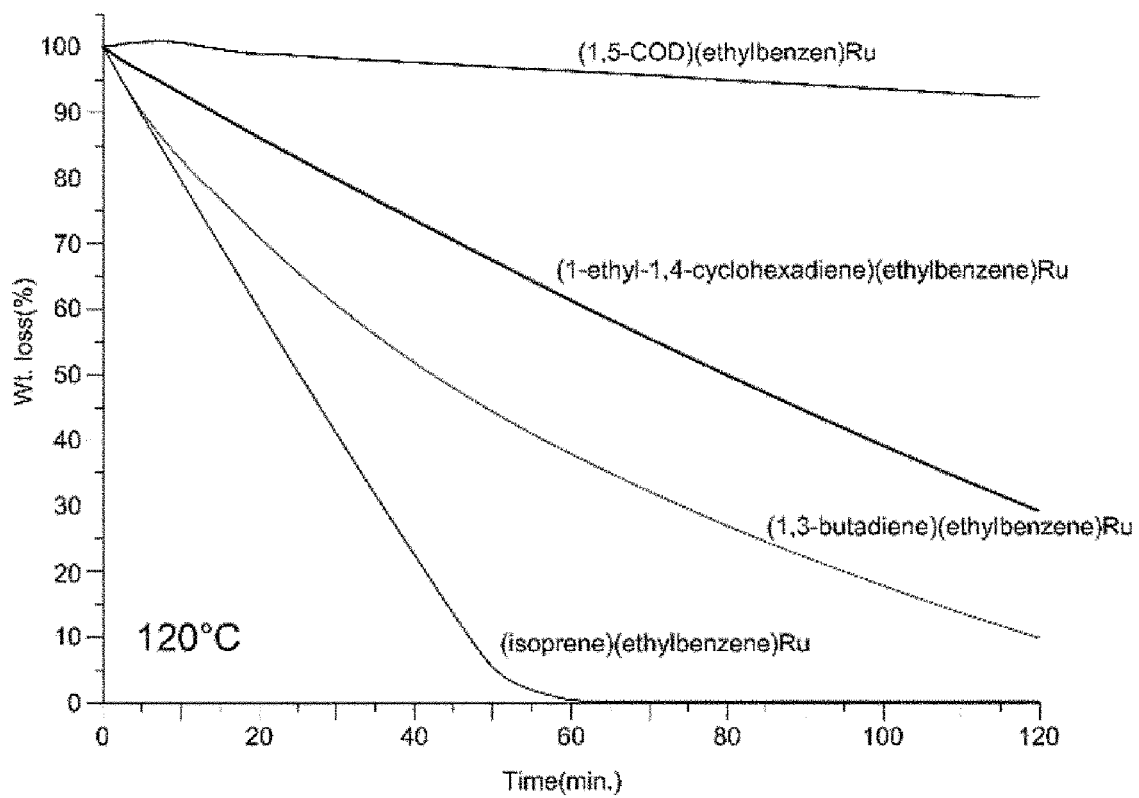
Figure 2D:
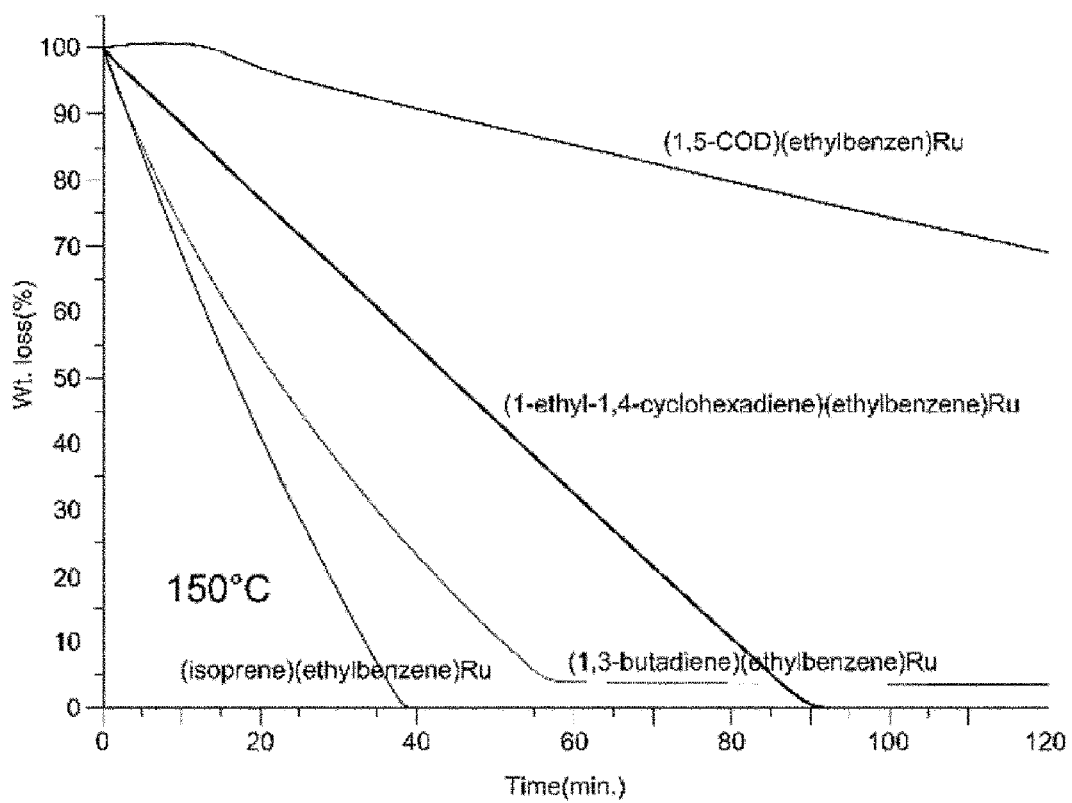
Figure 3:
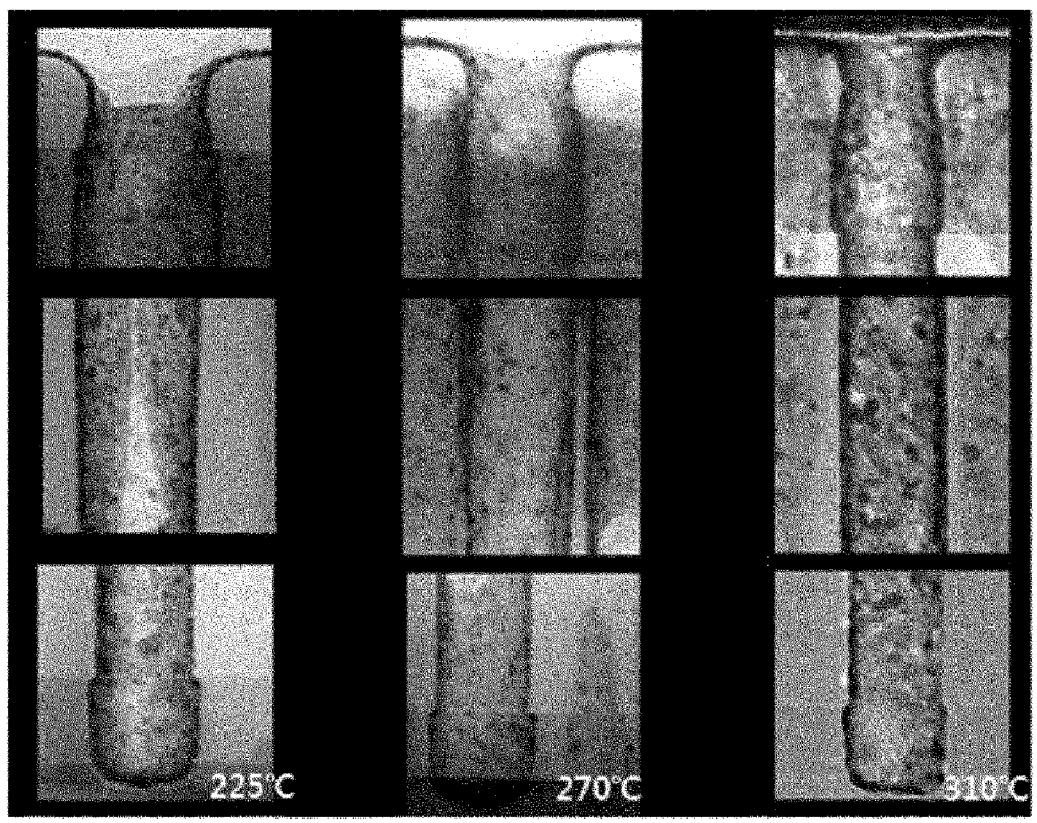
FIG. 3 shows scanning electron microscopic (SEM) images of a (1-ethyl-1,4-cyclohexadienyl)(ethylbenzene)ruthenium thin film.

A ruthenium compound represented by Chemical Formula 1 according to the present invention exhibits $T_{1/2}$ of 205-230° C. in a thermogravimetric analysis (TGA) spectrum, residue rate of 0-1.5%, constant weight loss in a temperature range of 80-120° C. and minimum residue rate of 0.1% or less within 90 minutes in an isothermal TGA spectrum at 150° C.

The ruthenium compound represented by Chemical Formula 1 according to the present invention may be prepared by reducing ruthenium(III) ion to ruthenium(II) ion as described in Scheme 1.

[Scheme 1]

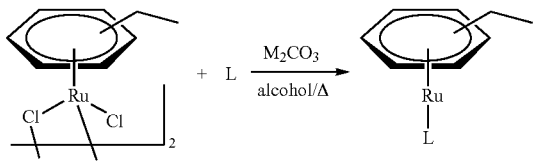

In Scheme 1, M is an alkali metal and L is a ligand selected from 1-ethyl-1,4-cyclohexadiene, 1,3-butadiene or isoprene.

The reduction reaction according to Scheme 1 is performed using an alcohol both as a reducing agent and a solvent in the presence of an alkali metal salt base. The alcohol used both as a reducing agent and a solvent may be a primary alcohol such as methanol, ethanol or n-propanol, a secondary alcohol such as isopropanol or isobutanol or a tertiary alcohol such as tert-butanol, having a $C_1$-$C_{10}$ alkyl group. Specifically, isopropanol may be used. The base may be specifically an alkali metal carbonate ($M_2CO_3$) such as lithium carbonate ($Li_2CO_3$), sodium carbonate ($Na_2CO_3$), potassium carbonate ($K_2CO_3$), etc.

Specifically, the reaction may be conducted under nitrogen ($N_2$) or argon (Ar) flow in order to prevent decomposition owing to moisture ($H_2O$), oxygen ($O_2$), etc.

The ruthenium compound represented by Chemical Formula 1 prepared by the above-described method is an organometallic compound existing as liquid at room temperature and having superior vaporizing property and thermal stability. Also, it is useful as a metal precursor compound for growing a high-purity ruthenium metal thin film or ruthenium oxide thin film by atomic layer deposition.

Accordingly, the present invention also provides a method for depositing a thin film, including forming a ruthenium metal thin film or a ruthenium oxide thin film by atomic layer deposition using the ruthenium compound represented by Chemical Formula 1.

The present invention relates to a method for depositing a thin film, including introducing the ruthenium compound using a carrier gas and reacting same with a reaction gas to grow the metal thin film or the metal oxide thin film on a substrate.

More specifically, the present invention relates to a method for depositing a thin film, wherein the deposition on the substrate may be performed at 180-500° C., specifically 200-350° C. More specifically, in the method for depositing a thin film of the present invention, the carrier gas or diluent gas may be one or more selected from argon (Ar), nitrogen ($N_2$), helium (He), hydrogen ($H_2$), oxygen ($O_2$) or ammonia ($NH_3$). The reaction gas may be one or more selected from a group consisting of hydrogen ($H_2$), steam ($H_2O$), ammonia ($NH_3$), hydrazine ($N_2H_4$), oxygen ($O_2$) and ozone ($O_3$).

More specifically, the present invention relates to a method for depositing a thin film, including depositing the ruthenium compound on a substrate using thermal energy or plasma or by applying a bias onto the substrate. More specifically, the present invention relates to a method for depositing a thin film, including transporting the ruthenium compound onto the substrate in liquid state using a method selected from a group consisting of bubbling, vapor-phase mass flow controller (MFC), direct liquid injection (DLI) and dissolving of the ruthenium compound in an organic solvent.

The present invention also provides a method for depositing a metal thin film or a metal oxide thin film on a substrate by atomic layer deposition (ALD), which includes: heating the ruthenium compound as a precursor to 20-200° C.; heating the substrate to 200-350° C. in vacuo or under inert atmosphere; introducing the precursor into a chamber using a carrier gas or a diluent gas; forming a precursor layer on the substrate by adsorbing the precursor onto the substrate; providing less than 1 minute for the precursor to form the layer on the substrate; removing unadsorbed excess precursor using an inert gas such as argon (Ar), nitrogen ($N_2$) or helium (He); providing less than 1 minute for removal of the excess precursor; introducing a reaction gas into the chamber to form a metal or metal oxide layer on the substrate; forming a metal thin film or a metal oxide thin film and a byproduct by allowing the reaction gas to react with the precursor layer formed on the substrate for less than 1 minute; and introducing an inert gas selected from argon (Ar), nitrogen ($N_2$) and helium (He) into the chamber for less than 1 minute to remove excess reaction gas and the byproduct, as a cycle of atomic layer deposition (ALD).

The present invention will be described in more detail through examples, but the scope of the present invention is not limited by them.

EXAMPLES

Example 1

Preparation of (1-ethyl-1,4-cyclohexadiene)(ethylbenzene)ruthenium

The dimer ethylbenzene ruthenium dichloride (150 g, 0.27 mol) and sodium carbonate ($Na_2CO_3$) (284 g, 2.68 mol) were weighed into a 2-L branched round flask. After adding 2-propanol (1000 mL) and stirring, 1-ethyl-1,4-cyclohexadiene (116 g, 1.07 mol) was added dropwise to the resulting mixture using a dropping funnel. Then, reaction was conducted for 10 hours under reflux using a reflux condenser. Upon completion of the reaction, the resulting solution was filtered and the solvent and a volatile byproduct were removed under reduced pressure. After extraction with hexane, the solvent and the volatile byproduct were removed again under reduced pressure to obtain a viscous, dark reddish-brown solution. This liquid was distilled under reduced pressure to obtain 139 g (yield: 82%) of (1-ethyl-1,4-cyclohexadiene)(ethylbenzene)ruthenium as viscous yellow liquid.

Boiling point (b.p.): 116° C./0.23 torr.
Vapor pressure (v.p.): 100° C./0.14 torr.
$^1$H-NMR ($C_6D_6$, ppm): δ 1.014 ([C$\underline{H}_3$CH$_2$C$_6$H$_7$]—Ru), m, 3H), 1.110 ([C$\underline{H}_3$CH$_2$C$_6$H$_5$]—Ru, m, 3H), 1.786 ([CH$_3$C$\underline{H}_2$C$_6$H$_7$][CH$_3$C$\underline{H}_2$C$_6$H$_5$]—Ru, m, 4H), 2.128 ([CH$_3$CH$_2$C$_6$$\underline{H}_7$]—Ru, m, 4H), 3.018 ([CH$_3$CH$_2$C$_6$$\underline{H}_7$]—Ru, s, 1H), 3.085 ([CH$_3$CH$_2$C$_6$$\underline{H}_7$]—Ru, s, 2H), 4.918 ([C$_2$H$_5$C$_6$$\underline{H}_5$]—Ru, m, 5H).

Example 2

Preparation of (1,3-butadiene)(ethylbenzene)ruthenium

The dimer ethylbenzene ruthenium dichloride (100 g, 0.18 mol) and sodium carbonate ($Na_2CO_3$) (114 g, 1.08 mol) were weighed into a 1-L branched round flask. After adding 2-propanol (500 mL) and stirring, 1,3-butadiene (250 g, 4.62 mol) was bubbled into the resulting mixture. Then, reaction was conducted for 2 days under reflux using a reflux condenser. Upon completion of the reaction, the resulting solution was filtered and the solvent and a volatile byproduct were removed under reduced pressure. After extraction with hexane, the solvent and the volatile byproduct were removed again under reduced pressure to obtain a viscous, dark reddish-brown solution. This liquid was distilled under reduced pressure to obtain 59 g (yield: 57%) of (1,3-butadiene)(ethylbenzene)ruthenium as viscous yellow liquid.

Boiling point (b.p.): 88° C./1.2 torr.
$^1$H-NMR ($C_6D_6$, ppm): δ 0.286 ([CH$_2$=CHCH=CH$_2$]—Ru, d, 2H), 0.958 ([CH$_3$CH$_2$C$_6$H$_5$]—Ru, tr, 3H), 1.940 ([CH$_2$=CHCH=CH$_2$]—Ru, d, 2H), 2.044 ([CH$_3$CH$_2$C$_6$H$_5$]—Ru, q, 2H), 4.776 ([CH$_3$CH$_2$C$_6$H$_5$]—Ru, m, 2H), 4.900 ([CH$_3$CH$_2$C$_6$H$_5$]—Ru, m, 1H, [CH$_2$=CHCH=CH$_2$]—Ru, m, 2H), 4.984 ([CH$_3$CH$_2$C$_6$H$_5$]—Ru, m, 2H).

Example 3

Preparation of (isoprene)(ethylbenzene)ruthenium

The dimer ethylbenzene ruthenium dichloride (20 g, 0.036 mol) and sodium carbonate ($Na_2CO_3$) (13.09 g, 0.12 mol) were weighed into a 1-L branched round flask. After adding 2-propanol (150 mL) and stirring, isoprene (12.36 g, 0.18 mol) was added dropwise to the resulting mixture using a dropping funnel. Then, reaction was conducted for a day under reflux using a reflux condenser. Upon completion of the reaction, the resulting solution was filtered and the solvent and a volatile byproduct were removed under reduced pressure. After extraction with hexane, the solvent and the volatile byproduct were removed again under reduced pressure to obtain a viscous, dark reddish-brown solution. This liquid was distilled under reduced pressure to obtain (8.51 g, yield: 37%) of (isoprene)(ethylbenzene)ruthenium as viscous yellow liquid.

Boiling point (b.p.): 118° C./0.5 torr.
$^1$H-NMR ($C_6D_6$, ppm): δ 0.175 ([CH$_2$=CHCH$_3$C=CH$_2$]—Ru, d, 1H), 0.377 ([CH$_2$=CHCH$_3$C=CH$_2$]—Ru, s, 1H), 0.976 ([CH$_3$CH$_2$C$_6$H$_5$]—Ru, tr, 3H), 1.894 ([CH$_2$=CHCH$_3$C=CH$_2$]—Ru, d, 1H), 1.983 ([CH$_2$=CHCH$_3$C=CH$_2$]—Ru, m, 3H, [CH$_2$=CHCH$_3$C=CH$_2$]—Ru, m, 1H, [CH$_3$CH$_2$C$_6$H$_5$]—Ru, m, 2H), 4.761 ([CH$_2$=CHCH$_3$C=CH$_2$]—Ru, tr, 1H, [CH$_3$CH$_2$C$_6$H$_5$]—Ru, tr, 1H), 4.815 ([CH$_3$CH$_2$C$_6$H$_5$]—Ru, d, 1H), 4.859 ([CH$_3$CH$_2$C$_6$H$_5$]—Ru), tr, 1H), 4.926 ([CH$_3$CH$_2$C$_6$H$_5$]—Ru, tr, 1H), 4.994 ([CH$_3$CH$_2$C$_6$H$_5$]—Ru, tr, 1H).

TEST EXAMPLES

Test Example 1

Comparison of Thermal Stability of Ruthenium Compounds

Thermogravimetric analysis (TGA) result of the ruthenium compounds prepared in Examples 1-3 is shown in Table 1 and FIG. 1.

In Table 1 and FIG. 1, the thermal stability of the ruthenium compounds of the present invention is compared with that of (1,5-cyclooctadienyl)(ethylbenzene)ruthenium represented by Chemical Formula A, which is disclosed in Korean Patent Publication No. 2010-60482. As seen from Table 1 and FIG. 1, the compounds represented by Chemical Formula 1 according to the present invention have high vapor pressure and are thermally stable as compared to the compound represented by Chemical Formula A.

TABLE 1

|  | Reference compound (Chemical Formula A) | Example 1 | Example 2 | Example 3 |
|---|---|---|---|---|
| $T_{1/2}$ (° C.) | 247 | 230 | 203 | 205 |
| Residue rate (%) | 6 | 1.5 | 1.47 | 0 |

Also, as seen from the isothermal TGA result in FIG. 2, all the precursor compounds showed constant weight loss in the temperature range of 80-120° C. without decomposition, suggesting that they have vaporizing properties sufficient for atomic layer deposition (ALD). The isothermal TGA result at 150° C. revealed that the compounds represented by Chemical Formula 1 according to the present invention showed rapid vaporization and decrease of the precursor residue rate to 0.1% or lower in 90 minutes whereas the compound represented by Chemical Formula A still showed constant weight loss of the precursor. Accordingly, it was confirmed that the ruthenium compounds of the present invention are advantageous in forming high-purity ruthenium metal thin film or ruthenium oxide thin film without particle contamination caused by thermal decomposition or contamination by impurities such as carbon.

Test Example 2

Comparison of Physical Properties of Ruthenium Thin Films

Ruthenium thin films were prepared by atomic layer deposition using the ruthenium compounds of the present invention. As a substrate for the deposition, a patterned SiO2 wafer of a trench structure having a pitch of ~85 nm at the top portion and an aspect ratio of ~32. A comparative experiment was conducted to evaluate the characteristics of the ruthenium compounds and thin films under the same conditions. The result is shown in Table 2.

[Deposition Conditions]
Precursor: ruthenium compound of Example 1, 2 or 3
Precursor feed temperature: 130-160° C.
Substrate: patterned wafer of a trench structure having a pitch of ~85 nm at the top portion and an aspect ratio of ~32
Substrate temperature: 180-310° C.
Number of pulsing/purge/O$_2$/pulsing/purge cycles: 11 cycles

TABLE 2

| | | Substrate temperature (° C.) | | | |
|---|---|---|---|---|---|
| | | 180 | 225 | 270 | 310 |
| Example 1 | Growth rate per cycle (nm/cycle) | 0.065 | 0.07 | 0.08 | 0.153 |
| | Specific resistance (μΩ · cm) | 2750 | 42 | 37 | 40 |
| | Cotability (%) | — | ~100 | ~80 | ~75 |
| Example 2 | Growth rate per cycle (nm/cycle) | 0.07 | 0.08 | 0.09 | 0.16 |
| | Specific resistance (μΩ · cm) | 2720 | 40 | 38 | 39 |
| | Cotability (%) | — | ~100 | ~80 | ~80 |
| Example 3 | Growth rate per cycle (nm/cycle) | 0.07 | 0.075 | 0.08 | 0.154 |
| | Specific resistance (μΩ · cm) | 2740 | 41 | 37 | 39 |
| | Cotability (%) | — | ~100 | ~80 | ~80 |

The thin films prepared from the ruthenium compounds represented by Chemical Formula 1 according to the present invention had broad ALD windows in the temperature range of 180-310° C. They had a specific resistance of 37-42 μΩ·cm, suggesting that they can be used in next-generation memory devices. Also, scanning electron microscopic (SEM) images revealed that the ruthenium compounds represented by Chemical Formula 1 according to the present invention showed good step coverage of 80% at a deposition temperature of 270° C. and very good step coverage of 100% at 225° C., when applied to substrates of a trench structure having a pitch of ~85 nm at the top portion and an aspect ratio of ~32.

INDUSTRIAL APPLICABILITY

As described above, the ruthenium compound represented by Chemical Formula 1 according to the present invention has physical properties appropriate for deposition of ruthenium metal thin film or ruthenium oxide thin film. In particular, since the ruthenium compound represented by Chemical Formula 1 according to the present invention has high thermal stability and high vapor pressure that are not degraded even under continuous heating, it can be usefully used in semiconductor manufacturing using atomic layer deposition (ALD).

The invention claimed is:

1. A method of depositing a ruthenium (Ru) metal thin film or ruthenium oxide (RuO$_2$) thin film comprising:
a ruthenium compound used for depositing metallic Ru or RuO$_2$ thin film on a substrate via atomic layer deposition,
wherein the ruthenium compound represented by Chemical Formula 1:

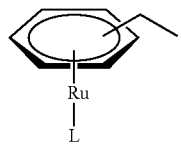

[Chemical Formula 1]

wherein L is a ligand selected from the group consisting of 1-ethyl-1,4-cyclohexadiene, 1,3-butadiene, and isoprene.

2. The method of claim 1, wherein the ruthenium compound is transferred to the substrate as a gas phase by using a method selected from the group consisting of a vaporization technique by heating the ruthenium compound in the range of 50° C. to 120° C., a liquid transfer technique by direct liquid injection (DLI), and a technique by dissolving the ruthenium compound in an organic solvent.

3. The method of claim 2, wherein the method is performed using atomic layer deposition comprising 4 steps from (a) to (d) as one cycle:
(a) introducing a precursor into a chamber as the gas phase using a transfer gas or a diluent gas selected from the group consisting of argon (Ar), nitrogen (N$_2$), and helium (He);
forming a precursor layer on the substrate by adsorbing the precursor onto the substrate;
providing a time period of less than 1 minute during which the precursor layer is formed on the substrate;
(b) removing excessive precursor that was not adsorbed onto the substrate by using an inert gas selected from the group consisting of argon (Ar), nitrogen (N$_2$), and helium (He);
providing a time period of less than 1 minute during which the excessive precursor is removed;
(c) introducing one of reaction gases or any mixture of the reaction gases selected from the group consisting of hydrogen (H$_2$), ammonia (NH$_3$), hydrazine (N$_2$H$_4$), water vapor (H$_2$O), ozone (O$_3$), and oxygen (O$_2$) into the chamber to form a ruthenium metal layer or a ruthenium oxide layer on the substrate;
forming a ruthenium metal thin film or a ruthenium oxide thin film and by-products by reacting the reaction gas with the precursor layer formed on the substrate for 1 minute or less; and
(d) introducing the inert gas selected from the group consisting of argon (Ar), nitrogen (N$_2$), and helium (He) into the chamber for 1 minute or less in order to remove excessive reaction gas and the by-products.

4. The method of claim 1, wherein the substrate temperature is in the range of 200° C. to 350° C.

5. The method of claim 1, wherein a reaction gas for depositing the ruthenium oxide thin film on the substrate comprises one selected from the group consisting of water vapor (H$_2$O), oxygen (O$_2$), and ozone (O$_3$).

6. The method of claim 1, wherein a reaction gas for depositing the ruthenium metal thin film on the substrate comprises one selected from the group consisting of hydrogen (H$_2$), ammonia (NH$_3$), hydrazine (N$_2$H$_4$), ozone (O$_3$), and oxygen (O$_2$).

* * * * *